(12) United States Patent
Ionkin et al.

(10) Patent No.: US 7,737,277 B2
(45) Date of Patent: Jun. 15, 2010

(54) ELECTROLUMINESCENT BIS-CYCLOMETALLED IRIDIUM COMPOUNDS AND DEVICES MADE WITH SUCH COMPOUNDS

(75) Inventors: Alex Sergey Ionkin, Kennett Square, PA (US); William J. Marshall, Wilmington, DE (US); Ying Wang, Wilmington, DE (US); Viacheslav A. Petrov, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 691 days.

(21) Appl. No.: 11/430,473

(22) Filed: May 8, 2006

(65) Prior Publication Data

US 2007/0259205 A1 Nov. 8, 2007

(51) Int. Cl.
C09K 11/06 (2006.01)
H01L 51/54 (2006.01)
(52) U.S. Cl. .............. 546/4; 546/6; 548/106; 428/917; 313/504; 257/E51.044
(58) Field of Classification Search .................. None
See application file for complete search history.

(56) References Cited

U.S. PATENT DOCUMENTS

| 5,247,190 | A | 9/1993 | Friend et al. | |
|---|---|---|---|---|
| 5,408,109 | A | 4/1995 | Heeger et al. | |
| 5,552,678 | A | 9/1996 | Tang et al. | |
| 2001/0019782 | A1* | 9/2001 | Igarashi et al. | 428/690 |
| 2002/0182441 | A1* | 12/2002 | Lamansky et al. | 428/690 |
| 2002/0190250 | A1 | 12/2002 | Grushin et al. | |
| 2003/0059646 | A1* | 3/2003 | Kamatani et al. | 428/690 |
| 2003/0173896 | A1* | 9/2003 | Grushin et al. | 313/506 |

FOREIGN PATENT DOCUMENTS

| EP | 0 443 861 B1 | 8/1991 |
|---|---|---|
| WO | WO 02/02714 A2 | 1/2002 |

OTHER PUBLICATIONS

M.A. Baldo et. al., Very High-Efficiency Green Organic Light-Emitting Devices Based on Electrophosphorescence, Appl. Phys. Lett., 1999, vol. 75:4-6.
Peter Djurovich et. al., Ir(III) Cyclometalated Complexes as Efficient Phosphorescent Emitters in Polymer Blend and Organic LEDs, Polymer Preprints, 2000, vol. 41:770.
Olivier Lohse et al., "The Palladium Catalysed Suzuki Coupling of 2- and 4- Chloropyridines", Synlett, 1999, pp. 45-48.
John Markus, Electronics and Nucleonics Dictionary (McGraw-Hill), 1966, pp. 470 and 476.
Y. Wang, "Photoconductive Polymers", Kirk-Othmer Encyclopedia of Chemical Technology, Fourth Edition, vol. 18, 1996, pp. 837-860.
Vladimir V. Grushin et al., "Facile Prepreparation and Synthetic Applications of LiCH2C(CF3)2OLi", Journal of Fluorine Chemistry, 117, 2002, pp. 121-129.
Von Heinrich Hellman et al., "Hydroxymethyl-Phosphine, Hydroxymethyl-Phosphoniumsalze und Chlormethyl-Phosphoniumsalze", Liebigs Ann. Chem., Bd 659, pp. 49-63, 1962.

* cited by examiner

*Primary Examiner*—Marie R. Yamnitzky
(74) *Attorney, Agent, or Firm*—Gail D. Tanzer

(57) ABSTRACT

One embodiment of this invention is bis-cyclometalled electroluminescent complexes of iridium (III) according to Formula I. Another embodiment of this invention is electronic devices in which the active layer includes a bis-cyclometalled electroluminescent Ir(III) complex.

Formula I

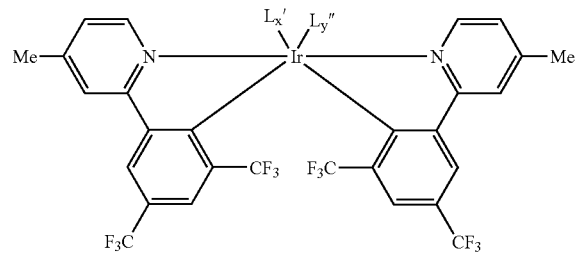

6 Claims, 1 Drawing Sheet

Figure 1 – Schematic of a light-emitting device
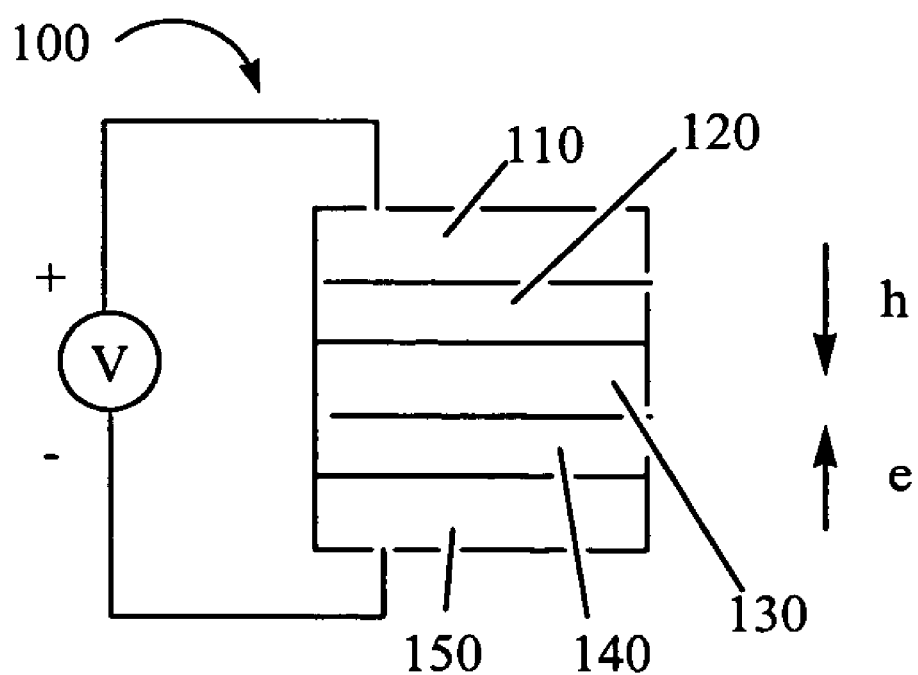

ELECTROLUMINESCENT BIS-CYCLOMETALLED IRIDIUM COMPOUNDS AND DEVICES MADE WITH SUCH COMPOUNDS

FIELD OF THE INVENTION

One embodiment of this invention is bis-cyclometalled electroluminescent complexes of iridium(III). Another embodiment of this invention is electronic devices in which the active layer includes an bis-cyclometalled electroluminescent Ir(III) complex.

BACKGROUND

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in U.S. Pat. No. 5,247,190, U.S. Pat. No. 5,408,109, and EP443 861. Complexes of 8-hydroxyquinolate with trivalent metal ions, particularly aluminum, have been extensively used as electroluminescent components, as has been disclosed in U.S. Pat. No. 5,552,678.

US 2002/0190250 discloses electroluminescent iridium compounds with fluorinated phenylpyridines, and devices made with such compounds.

Burrows and Thompson have reported that fac-tris(2-phenylpyridine) iridium can be used as the active component in organic light-emitting devices (*Appl. Phys. Lett.* 1999, 75, 4.). The performance is maximized when the iridium compound is present in a host conductive material. Thompson has further reported devices in which the active layer is poly(N-vinyl carbazole) doped with fac-tris[2-(4',5'-difluorophenyl)pyridine-$C^{'2}$,N]iridium(III) (Polymer Preprints 2000, 41(1), 770). Electroluminescent iridium complexes having fluorinated phenylpyridine, phenylpyrimidine, or phenylquinoline ligands have been disclosed in WO 02/02714.

However, there is a continuing need for electroluminescent compounds.

SUMMARY OF THE INVENTION

One aspect of this invention is a composition represented by Formula I:

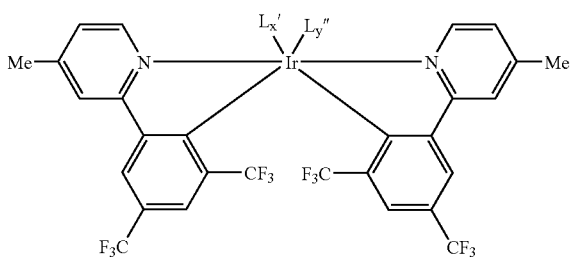

Formula I wherein:
L'=a bidentate ligand selected from β-enolate ligands, non-fluorinated β-phosphinoalkoxide ligands, 1,3-diphosphine ligands;
L"=a monodentate ligand selected from halides, carbon monooxide, hydrido, hydroxy ligands;
X=1, y=0, if L is a bidentate ligand;
X=0, y=2, if L is a monodentate ligand;
with the proviso that the iridium is hexacoordinate.

DESCRIPTION OF THE DRAWINGS

FIG. 1 is a schematic diagram of a light-emitting device (LED).

DETAILED DESCRIPTION

Definition of Terms. As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, where "a" and "b" represent different coordinating atoms, having octahedral geometry, in which the three "a" atoms are all adjacent, i.e. at the corners of one face of the octahedron. The term "meridional" is intended to mean one isomer of a complex, $Ma_3b_3$, having octahedral geometry, in which the three "a" atoms occupy three positions such that two are trans to each other. The term "hexacoordinate" is intended to mean that six groups or points of attachment are coordinated to a central metal. The phrase "adjacent to," when used to refer to layers in a device does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. In the Formulae and Equations, the letters L, R, Y, and Z are used to designate atoms or groups, which are defined within. All other letters are used to designate conventional atomic symbols. The term "(H+F)" is intended to mean all combinations of hydrogen and fluorine, including completely hydrogenated, partially fluorinated or perfluorinated substituents. The term "alkylaryl" denotes an alkyl-substituted aryl group.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Ir(III) compounds. The present invention is directed to iridium compounds (generally referred as "Ir(III) compounds") represented by Formula I:

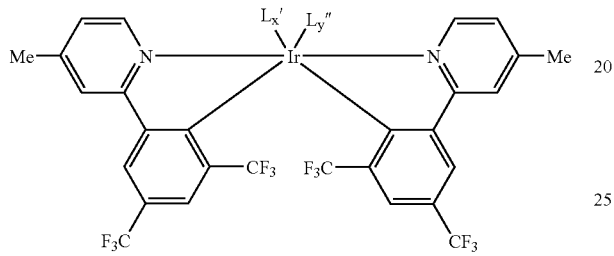

wherein:
L'=a bidentate ligand selected from β-enolate ligands, non-fluorinated β-phosphinoalkoxide ligands, 1,3-diphosphine ligands;
L"=a monodentate ligand selected from halides, carbon monooxide, hydrido, hydroxy ligands;
X=1, y=0, if L is a bidentate ligand;
X=0, y=2, if L is a monodentate ligand;
with the proviso that the iridium is hexacoordinate.

Specific examples of the iridium compounds include:

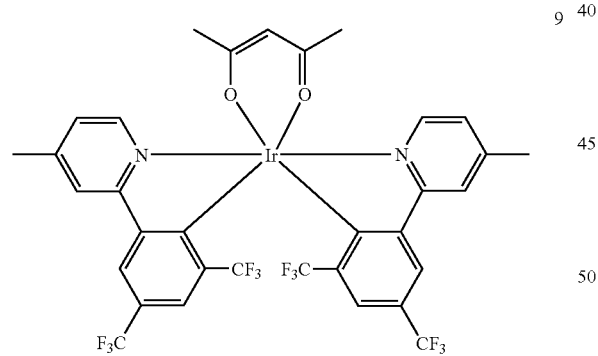

9

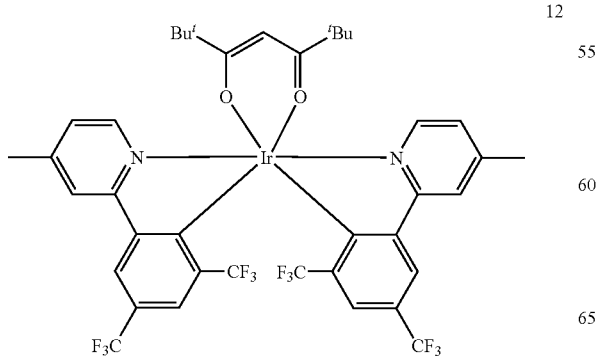

12

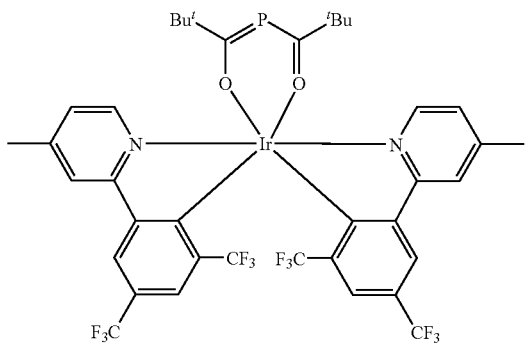

15

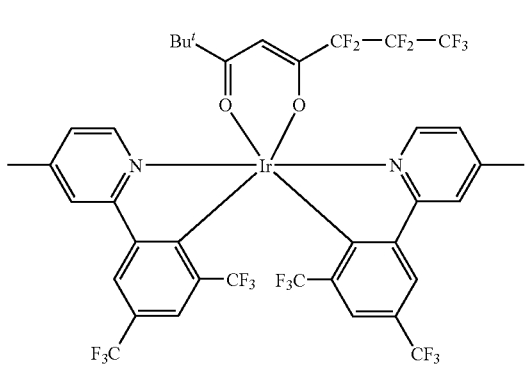

17

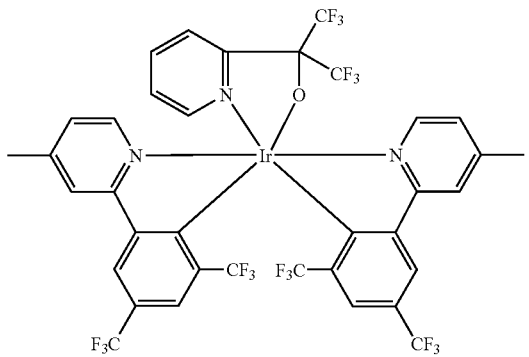

19

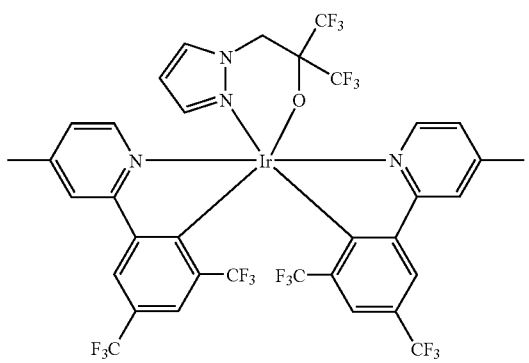

21

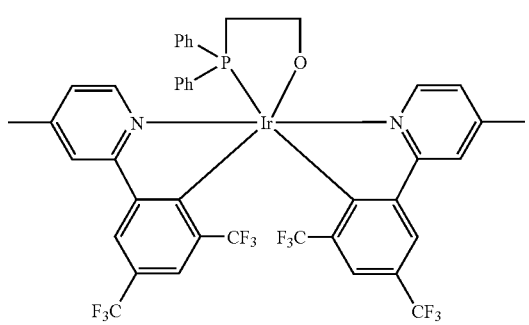

23

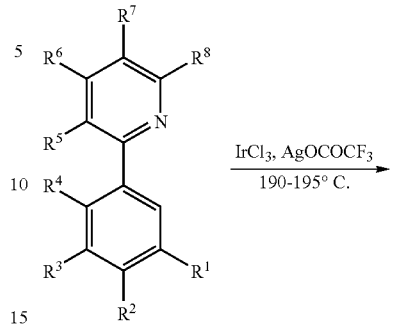

Eq. 1

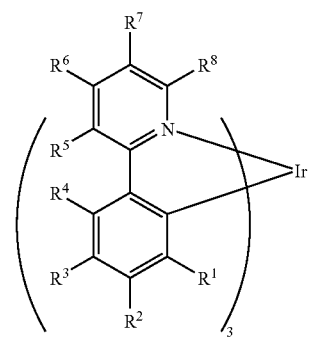

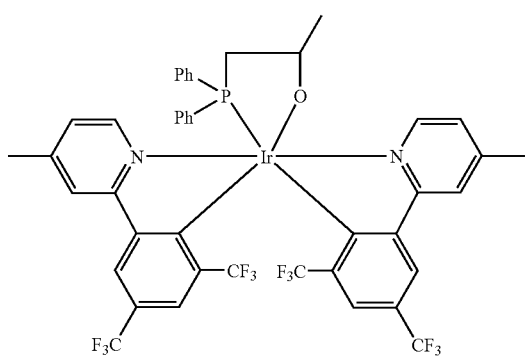

Monodentate ligand L" can be anionic or nonionic. Anionic ligands include, but are not limited to, H⁻ ("hydride") and ligands having C, O or S as coordinating atoms. Coordinating groups include, but are not limited to alkoxides, carboxylates, thiocarboxylates, dithiocarboxylates, sulfonates, thiolates, carbamates, dithiocarbamates, thiocarbazone anions, or sulfonamide anions. In some cases, ligands listed above as L', such as β-enolates and non-fluorinated phosphinoalkoxides, can act as monodentate ligands. The monodentate ligand can also be a coordinating anion such as halide, nitrate, sulfate, or hexahaloantimonate.

It is understood that there is free rotation about the bond between the two aromatic ring systems. However, for the discussion herein, the compounds are described in terms of one orientation.

Preparation of complexes and precursors. The substituted 2-phenylpyridines and related compounds, as shown in Formula II above, are prepared in good to excellent yield using the Suzuki coupling of the substituted 2-chloropyridine (or chloroquinoline or choloroisoquinoline) with arylboronic acid, as described in O. Lohse, P. Thevenin, E. Waldvogel *Synlett*, 1999, 45-48.

The 2-phenylpyridines and related compounds can be used for the synthesis of cyclometalated iridium complexes. One method uses commercially available iridium trichloride hydrate and silver trifluoroacetate. The reactions are generally carried out with an excess of the appropriate 2-phenylpyridine (or pyrimidine or quinoline), without a solvent, in the presence of 3 equivalents of AgOCOCF₃. This reaction is illustrated in Equation (1) below:

Tris-cyclometalated iridium complexes having Formula I where m=3, can be isolated, purified, and fully characterized by elemental analysis, $^1$H and $^{19}$F $^{31}$P NMR spectral data, and, for selected compounds, single crystal X-ray diffraction. In some cases, mixtures of isomers are obtained. Often the mixture can be used without isolating the individual isomers.

Bis-cyclometalated iridium complexes having Formula I, can, in some cases, be isolated from the reaction mixture using the same synthetic procedures as preparing the tris-cyclometalated complexes above. The complexes can also be prepared by first preparing an intermediate iridium dimer

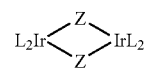

where L is the same or different and is a phenylpyridine, phenylquinoline or phenylisoquinoline ligand, and Z is Cl or OR$^{16}$, where R$^{16}$ is H, CH₃, or C₂H₅. The iridium dimers can generally be prepared by first reacting iridium trichloride hydrate with the 2-phenylpyridine and optionally adding NaOR$^{16}$.

In an improved process for preparing bis-cyclometalated iridium complexes, the chloro-bridged iridium dimer is prepared by reacting iridium (III) chloride trihydrate with the appropriate ligand precursor in trimethylphosphate.

Mono-cyclometalated iridium complexes of the invention can, in some cases, be isolated from reaction mixtures formed by the above-described processes. Such mono-cyclometalated species can be favored by use of phosphine-containing ligands such as that shown in Formula VI and by using a stoichiometric excess of such ligands (>2 equivalents per Ir). These materials can be isolated from the reaction mixture by standard techniques, such as chromatography on silica with methylene chloride as eluent.

Electronic Device

One embodiment of this invention is an electronic device comprising at least one photoactive layer positioned between two electrical contact layers, wherein the at least one layer of the device includes the iridium complex of the invention. Devices frequently have additional hole-transport and electron-transport layers. A typical structure is shown in FIG. 1. The device 100 has an anode layer 110 and a cathode layer 150. Adjacent to the anode is a layer 120 comprising hole-transport material. Adjacent to the cathode is a layer 140 comprising an electron-transport material. Between the hole-transport layer and the electron-transport layer is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, phototubes, and photovoltaic cells, as these terms are described by John Markus in *Electronics and Nucleonics Dictionary*, 470 and 476 (McGraw-Hill, Inc. 1966).

The iridium compounds of the invention are particularly useful as the photoactive material in layer 130, or as electron-transport material in layer 140. The iridium complexes of the invention can be used as the light-emitting material in diodes. Additional materials can be present in the emitting layer with the iridium compound. A diluent or host material can also be added. Suitable diluents include charge transport materials, processing aids and inert matrix materials. The diluent can be polymeric materials, small molecule or mixtures thereof. The diluent may improve the physical or electrical properties of films containing the iridium compound, may decrease self-quenching in the iridium compounds described herein, and/or may decrease the aggregation of the iridium compounds described herein. Non-limiting examples of suitable polymeric materials include poly(N-vinyl carbazole) and polysilane. Non-limiting examples of suitable small molecules includes 4,4'-N,N'-dicarbazole biphenyl and tertiary aromatic amines. When a diluent is used, the iridium compound is generally present in a small amount. In one embodiment, the iridium compound is less than 20% by weight, based on the total weight of the layer; in another embodiment, the iridium compound is less than 10% by weight.

In some embodiments, the iridium complexes may be present in more than one isomeric form, or mixtures of different complexes may be present. It will be understood that in the above discussion of OLEDs, the term "the iridium compound" is intended to encompass mixtures of compounds and/or isomers.

The other layers in the OLED can be made of any materials which are known to be useful in such layers. The anode 110, is an electrode that is particularly efficient for injecting positive charge carriers. For example, it can be made of materials containing a metal, mixed metals, alloys, metal oxides or mixed-metal oxides, or it can be a conducting polymer. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1-18 (CRC Handbook of Chemistry and Physics, 81$^{st}$ Edition, 2000). The anode 110 may also comprise an organic material such as polyaniline as described in "Flexible light-emitting diodes made from soluble conducting polymer," *Nature* vol. 357, pp 477-479 (11 Jun. 1992). At least one of the anode and cathode should be at least partially transparent to allow the generated light to be observed.

Examples of hole-transport materials for layer 120 have been summarized for example, in Kirk-Othmer Encyclopedia of Chemical Technology, Fourth Edition, Vol. 18, p. 837-860, 1996, by Y. Wang. Both hole-transporting molecules and polymers can be used. Commonly used hole-transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl-]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)4,4'-diamine (TTB), and porphyrinic compounds, such as copper phthalocyanine. Commonly used hole-transporting polymers are polyvinylcarbazole, (phenylmethyl)polysilane, and polyaniline. It is also possible to obtain hole-transporting polymers by doping hole-transporting molecules such as those mentioned above into polymers such as polystyrene and polycarbonate.

Examples of electron-transport materials for layer 140 include metal chelated oxinoid compounds, such as tris(8-hydroxyquinolato)aluminum (Alq$_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron-transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, can be surface treated to increase charge carrier transport efficiency. The choice of materials for each of the component layers is preferably determined by balancing the goals of providing a device with high device efficiency.

It is understood that each functional layer can be made up of more than one layer.

The device can be prepared by sequentially vapor depositing the individual layers on a suitable substrate. Substrates such as glass and polymeric films can be used. Conventional vapor deposition techniques can be used, such as thermal evaporation and chemical vapor deposition. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole-transport layer 120, 50-1000 Å, preferably 200-800 Å; light-emitting layer 130, 10-1000 Å, preferably 100-800 Å; electron-transport layer 140, 50-1000 Å, preferably 200-800 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the iridium compounds of the invention, can be further improved by optimizing the other layers in the device. For example, more efficient cathodes such as Ca, Ba or LiF can be used. Shaped substrates and novel hole-transport materials that result in a reduction in operating voltage or increase quantum efficiency are also applicable. Additional layers can also be added to tailor the energy levels of the various layers and facilitate electroluminescence.

The iridium complexes of the invention are photoluminescent and may be useful in applications other than OLEDs. For example, organometallic complexes of iridium have been used as oxygen sensitive indicators, as phosphorescent indicators in bioassays, and as catalysts. The bis-cyclometalated complexes can be used to synthesize tris-cyclometalated complexes where the third ligand is the same or different.

EXAMPLES

The following examples illustrate certain features and advantages of the present invention. They are intended to be illustrative of the invention, but not limiting. All percentages are by weight, unless otherwise indicated.

The following chemicals used in the Examples below were purchased from Sigma-Aldrich Inc. (St. Louis, Mo.): 3,5-bis-trifluoromethylphenylboronic acid, 2-chloro-4-methylpyridine, cesium fluoride, 1,4-dioxane, lithium 2,4-pentanedionate, lithium 2,2,6,6-tetramethyl-heptane-3,5-dionate, trimethylphosphate, rubidium hydroxide in water, benzoylformic acid, di-t-butylchlorophosphine, (trimethylsilylmethyl)lithium, tris(trimethylsilyl)phosphine, pivaloyl chloride, 2,2-dimethyl-6,6,7,7,8,8,8-heptafluoro-3,5-octadione tris(dibenzylideneacetone)dipalladium(0); trimethylphosphate; "AIQ"; and "DPA". The iridium(III) chloride trihydrate used in the Examples below was purchased from Alfa Aesar (Ward Hill, Mass.). The preparation of MPMP is disclosed in U.S. Pat. No. 3,739,000.

General Procedures. All the operations related to catalysts were carried out under an argon atmosphere using standard Schlenk techniques. Anhydrous solvents were used in the reactions. Solvents were distilled from drying agents or passed through alumina columns under an argon or nitrogen atmosphere. 2,2-Bis(trifluoromethyl)oxirane is a DuPont product. 2-[(Diphenylphosphanyl)-methyl]-1,1,1,3,3,3-hexafluoro-propan-2-ol was synthesized by the known addition of diphenylphosphine to 2,2-bis(trifluoromethyl)oxirane as described in Grushin, V. V.; Marshall, W. J.; Halliday, G. A.; Davidson, F.; Petrov, V. A. *J. Fluorine Chem.*, 2002, 117, 121. 2-Diphenylphosphanyl-ethanol and 1-diphenylphosphanyl-propan-2-ol were synthesized by the reaction of diphenylphosphine with appropriate epoxy compounds as described in Issleib, K.; Reischel. R. *Chem. Ber.* 1965, 98, 2086. Diphenylphosphanyl-methanol was prepared by reaction of diphenylphosphine and formaldehyde as described in Hellmann, H.; Bader, J.; Birkner, H.; Schumacher. O. Ann. 1962, 659, 49.

Di-tert-butyl-trimethylsilanylmethyl-phosphane (5). 50.00 g (0.277 mol) of Di-t-butylchlorophosphine, 304 ml of 1.0 M pentane solution of (trimethylsilylmethyl)lithium and 150 ml of THF) were refluxed under argon for 3 days. The reaction mixture was allowed to cool off to RT and an aqueous solution of ammonium chloride was added slowly. The organic phase was separated, and dried with magnesium sulfate. After removal of the solvent, the product was purified by distillation in vacuum. The yield of di-tert-butyl-trimethylsilanylmethyl-phosphane was 55.32 g (86%) with b.p. 50-52° C./0.5 mm. $^{31}$P NMR ($C_6D_6$)+20.05 ppm. $^1$H NMR ($C_6D_6$) 0.01 (s, 9H, SiMe$_3$), 0.23 (d, 2H, $^2J_{PH}$=5.34 Hz, P—CH$_2$—SiMe$_3$), 0.91 (s, 9H, Me$_3$C), 0.93 (s, 9H, Me$_3$C). Anal. Calcd. for $C_{12}H_{29}$PSi: C, 62.01; H, 12.58; P, 13.33. Found: C, 61.89; H, 12.53; P, 13.25.

2-(3,5-Bis-trifluoromethyl-phenyl)-4-methyl-pyridine (1). 15.0 g (0.05815 mol) of 3,5-Bis-trifluoromethylphenylboronic acid 3, 7.42 g (0.05816 mol) of 2-chloro-4-methylpyridine 2, 17.43 g (0.1148 mol) of cesium fluoride 7, 0.53 g (0.000579 mol) of tris(dibenzylideneacetone) dipalladium(0) 6, 0.33 g (0.00142 mol) of di-tert-butyl-trimethylsilylmethyl-phosphane 5 and 100 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/0.5. Yield of 2-(3,5-bis-trifluoromethyl-phenyl)4-methylpyridine 1 was 16.18 g (91%) as colorless liquid. $^1$H NMR (CDCl$_3$) 2.56 (s, 3H, Me), 7.11 (s, 1H, arom-H), 7.51 (s, 1H, arom-H), 7.90 (s, 1H, arom-H), 8.45-8.55 (m, 3H, arom-H). $^{19}$F NMR (CDCl$_3$) −63.35 (s, 3F, CF3), −63.36 (s, 3F, CF3). Anal. Calcd. for $C_{14}H_9F_6$N: C, 55.09; H, 2.97; N, 4.59. Found: C, 55.01; H, 3.12; N, 4.44.

Iridium, di-μ-chlorotetrakis[4,6-bis(trifluromethyl)-2-(4-methyl-2-pyridinyl-κN)phenyl-κC]di-, (8). 12.38 g (0.0406 mol) of 2-(3,5-Bis-trifluoromethyl-phenyl)-4-methyl-pyridine, 5.47 g (0.0155 mol) of iridium (III) chloride trihydrate, and 40 ml of trimethylphosphate were stirred at 90° C. for 6 hours under the flow of nitrogen. The formed precipitate was filtered and dried under 1.0-mm vacuum. The yield of the dimer was 16.96 g (84%) as yellow powder. The above crude chlorodimer was used "as it is" in the next steps.

Iridium, bis[4,6-bis(trifluromethyl)-2-(4-methyl-2-pyridinyl-κN)phenyl-κC](2,4-pentanedionato-κO,κO')-, (9). 2.5 g (0.00150 mol) of Iridium, di-μ-chlorotetrakis[4,6-bis(trifluromethyl)-2-(4-methyl-2-pyridinyl-κN)phenyl-κC]di-, 7.32 g (0.0687) lithium 2,4-pentanedionate, and 30 ml of THF were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC](2,4-pentanedionato-κO, κO')-, was 2.17 g (81%) as yellow solid with m.p. 351.48° C. $^1$H NMR (CD$_2$Cl$_2$) 1.60 (s, 6H, Me), 2.55 (s, 3H, Me), 5.30 (s, 1H, H—C═), 6.90-8.10 (m, 10H, arom-H). $^{19}$F NMR (CD$_2$Cl$_2$) −60.23 (s, 6F, CF3), −63.00 (s, 6F, CF3), Anal. Calcd. for $C_{33}H_{23}F_{12}IrN_2O_2$ (Exact Mass: 900.12): C, 44.05; H, 2.58; N, 3.11. Found: C, 44.01; H, 2.51; N, 2.88. Yield of iridium, [4,6-bis(trifluromethyl)-2-(4-methyl-2-pyridinyl-κN)phenyl-κC], [2-(4-methyl-2-pyridinyl-κN)-6-methyl-3-pyridinyl-κC],(2,4-pentanedionato-κO,κO')-, (10) was 0.34 g (15%) as yellow solid with no m.p. until 200° C. $^1$H NMR (CD$_2$Cl$_2$) 1.55 (br., 6H, Me), 2.45 (br., 3H, Me), 5.20 (s, 1H, H—C═), 6.90-8.10 (m, 9H, arom-H). $^{19}$F NMR (CD$_2$Cl$_2$)

−60.54 (s, 6F, CF3), −63.07 (s, 6F, CF3), Anal. Calcd. for $C_{31}H_{26}F_6IrN_3O_2$ (Exact Mass: 779.16): C, 47.81; H, 3.37; N, 5.40. Found: C, 47.83; H, 3.07; N, 5.36. Yield of iridium, dichloro,[4,4'-dimethyl-[2,2']bipyridinyl-κN1,κN1],(2,4-pentanedionato-κO,κO')-, (11) was 0.08 g (5%) as a few orange crystals with no m.p. until 200° C. $^1$H NMR (CD$_2$Cl$_2$) 1.55 (br., 6H, Me), 2.45 (br., 6H, Me), 5.21 (s, 1H, H—C=), 6.85-8.12 (m, 6H, arom-H). Anal. Calcd. for $C_{17}H_{19}Cl_2IrN_2O_2$ (Exact Mass: 546.05): C, 37.36; H, 3.50; N, 5.13. Found: C, 37.40; H, 3.73; N, 5.42.

Iridium, bis[4,6-bis(trifluromethyl)-2-(4-methyl-2-pyridinyl-κN)phenyl-κC](2,2,6,6-tetramethyl-3,5-heptanedionato-κO,κO')-, (12). 2.5 g (0.00150 mol) of Iridium, di-μ-chlorotetrakis[4,6-bis(trifluromethyl)-2-(4-methyl-2-pyridinyl-κN)phenyl-κC]di-, 5.91 g (0.0311) lithium 2,2,6,6-tetramethyl-heptane-3,5-dionate 13, and 30 ml of THF were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC](2,2,6,6-tetramethyl-3,5-heptanedionato-κO,κO')-, was 1.97 g (67%) as yellow solid with m.p. 306.53° C. $^1$H NMR (CD$_2$Cl$_2$) 0.80 (s, 18H t-Bu), 2.50 (s, 6H, Me), 5.40 (s, 1H, H—C=), 6.40-8.10 (m, 10H, arom-H). $^{19}$F NMR (CD$_2$Cl$_2$) −60.26 (s, 6F, CF3), −62.83 (s, 6F, CF3), Anal. Calcd. $C_{39}H_{35}F_{12}IrN_2O_2$ (Mol. Wt.: 983.91): C, 47.61; H, 3.59; N, 2.85. Found: C, 47.55; H, 3.60; N, 2.78. The structure was proven by X-ray analysis.

Iridium, bis[4,6-bis(trifluromethyl)-2-(4-methyl-2-pyridinyl-κN)phenyl-κC],((2,2-dimethyl-1-oxopropyl)phosphinato-O,O')-, (15). 1.0 g (0.0006 mol) of Iridium, di-μ-chlorotetrakis[4,6-bis(trifluromethyl)-2-(4-methyl-2-pyridinyl-κN)phenyl-κC]di-, 0.95 g (0.00345 mol) of dipivaloyltrimethylsilylphosphine 14, and 30 ml of THF were refluxed for 2 hours under argon atmosphere. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC],((2,2-dimethyl-1-oxopropyl)phosphinato-O,O')-, was 0.35 g (30%) as yellow solid with no m.p. until 200° C. $^1$H NMR (CD$_2$Cl$_2$) 0.75 (s, 18H, Me), 1.65 (s, 6H, Me), 6.00-8.10 (m, 10H, arom-H). $^{19}$F NMR (CD$_2$Cl$_2$) −59.51 (s, 6F, CF3), −62.11 (s, 6F, CF3). $^{31}$P NMR (CD$_2$Cl$_2$) 50.97. $^{13}$C NMR (CD$_2$Cl$_2$) (selected signals)+ 240.23 (d., $^1J_{CP}$=108.8 Hz, C=P). Anal. Calcd. for $C_{38}H_{34}F_{12}IrN_2O_2P$ (Mol. Wt.: 1001.86): C, 45.56; H, 3.42; N, 2.80. Found: C, 45.50; H, 3.79; N, 3.09. The structure was proven by X-ray analysis.

Iridium, bis[4,6-bis(trifluromethyl)-2-(4-methyl-2-pyridinyl-κN)phenyl-κC],(6,6,7,7,8,8,8-heptafluoro-2,2-dimethyl-3,5-octanedionato-κO,κO')-, (17). 1.0 g (0.0006 mol) of Iridium, di-μ-chlorotetrakis[4,6-bis(trifluromethyl)-2-(4-methyl-2-pyridinyl-κN)phenyl-κC]di-, 0.51 g (0.00172 mol) of 2,2-dimethyl-6,6,7,7,8,8,8-heptafluoro-3,5-octadione 16, 0.64 g (0.0062 mol) of rubidium hydroxide in 5 ml of water, and 40 ml of 1,2-dichloroetane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC],(6,6,7,7,8,8,8-heptafluoro-2,2-dimethyl-3,5-octanedionato-κO,κO')-, was 0.37 g (30%) as yellow solid with no m.p. until 200° C. $^1$H NMR (CD$_2$Cl$_2$) 0.80 (s, 9H, Me), 2.60 (s, 6H, Me), 5.70 (s, 1H, H—C=), 6.50-8.10 (m, 10H, arom-H). $^{19}$F NMR (CD$_2$Cl$_2$) −60.08.51 (s, 6F, CF3), −63.03 (s, 6F, CF3), −81.15 (s, 3F, CF3), −119.02 (m, 2F, CF2), −127.07 (m, 2F, CF2). Anal. Calcd. $C_{38}H_{26}F_{19}IrN_2O_2$ (Mol. Wt.: 1095.81): C, 41.65; H, 2.39; F, N, 2.56. Found: C, 41.66; H, 2.39; N, 2.72.

Iridium, bis[4,6-bis(trifluromethyl)-2-(4-methyl-2-pyridinyl-κN)phenyl-κC],[α,α-bis(trifluoromethyl)-2-pyridinemethanolato-κN1,κO2], (19). 0.9 g (0.00054 mol) of Iridium, di-μ-chlorotetrakis[4,6-bis(trifluromethyl)-2-(4-methyl-2-pyridinyl-κN)phenyl-κC]di-, 0.50 g (0.00203 mol) of 1,1,1,3,3,3-hexafluoro-2-pyridin-2-yl-propan-2-ol 18, 0.60 g (0.0059 mol) of rubidium hydroxide in 5 ml of water, and 40 ml of 1,2-dichloroethane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC],[α,α-bis(trifluoromethyl)-2-pyridinemethanolato-κN1,κO2], was 0.73 g (65%) as yellow solid with no m.p. until 200° C. $^1$H NMR (CD$_2$Cl$_2$) 2.40 (s, 6H, Me), 6.50-8.70 (m, 14H, arom-H). $^{19}$F NMR (CD$_2$Cl$_2$) −59.32 (s, 3F, CF3), −59.63 (s, 3F, CF3), −62.98 (s, 3F, CF3), −63.01 (s, 3F, CF3), −72.43 (s, 3F, CF3), −76.59 (s, 3F, CF3). Anal. Calcd. for $C_{36}H_{20}F_{18}IrN_3O$ (Mol. Wt.: 1044.75): C, 41.39; H, 1.93; N, 4.02. Found: C, 41.49; H, 2.11; N, 4.73.

1,1,1,3,3,3-Hexafluoro-2-pyrazol-1-ylmethyl-propan-2-ol (20). To the mixture of 13 g of KOH (pellets), 100 mL of THF 0.2 g of $(C_4H_9)_4N^+HSO_4^-$ pyrazole (13.6 g, 0.2 mol) of was added in one portion. The reaction mixture was agitated at ambient temperature for 1 h, cooled down to +5° C. and 38 g (0.21 mol) of 2,2-bis(trifluoromethyl)oxirane was slowly added (~1 h) at 5-15° C. Clear solution was agitated for another hour at 15° C. and ~100 mL 10% hydrochloric acid was added over 30 min period to the reaction mixture to bring pH to 3.5. The reaction mixture was diluted with 300 ml of water, extracted by dichloromethane (100 mL×2), extract was dried over MgSO$_4$, and the solvent was removed under reduced pressure to leave 47 g (95%) of white crystalline 1,1,1,3,3,3-hexafluoro-2-pyrazol-1-ylmethyl-propan-2-ol, m.p. 80° C. (from hexane, DSC), purity >99%.

$^1$H NMR (CDCl$_3$): 4.62 (2H, s), 6.31 (1H, t, 2 Hz), 7.24 (1H, br. s), 7.47 (1H, d, 2 Hz), 7.64 (1H, d, 2 Hz) ppm. $^{19}$F NMR (CDCl$_3$): −77.11 (s) ppm. $^{13}$C NMR (CDCl$_3$): 49.08 (hept, 2.2 Hz), 76.83 (hept., 29 Hz), 107 (s), 14.56 (q, 289 Hz), 132.10, 141.78 ppm. MS (m/z) 248 (M$^+$, $C_7H_6F_6N_2O^+$). Anal. Calc. for $C_7H_6F_6N_2O$: C, 33.88, H2.44, N, 11.11. Found: C, 33.90, H2.42, N, 11.29.

Iridium, bis[4,6-bis(trifluromethyl)-2-(4-methyl-2-pyridinyl-κN)phenyl-κC],[α,α-bis(trifluoromethyl)-2-pyrazol-1-ylmethyl-propan-2-olato-κN1,κO2], (21). 1.0 g (0.0006 mol) of Iridium, di-μ-chlorotetrakis[4,6-bis(trifluromethyl)-2-(4-methyl-2-pyridinyl-κN)phenyl-κC]di-, 0.43 g (0.00173 mol) of 1,1,3,3,3-hexafluoro-2-pyrazol-1-ylmethyl-propan-2-ol 20, 0.60 g (0.0059 mol) of rubidium hydroxide in 5 ml of water, and 40 ml of 1,2-dichloroetane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC],[α,α-bis(trifluoromethyl)-2-pyrazol-1-ylmethyl-propan-2-olato-κN1,κO2], was 0.74 g (59%) as yellow no m.p. until 200° C. $^1$H NMR (CD$_2$Cl$_2$) 2.50 (s, 6H, Me), 3.80 (s, 1H, CH2), 4.30 (s, 1H, CH2), 6.10-8.60 (m, 13H, arom-H). $^{19}$F NMR (CD$_2$Cl$_2$) −59.13 (s, 3F, CF3), −59.35 (s, 3F, CF3), −62.96 (s, 3F, CF3), −63.03 (s, 3F, CF3), −75.17 (s, 3F, CF3), −78.60 (s, 3F, CF3). Anal. Calcd. for $C_{35}H_{21}F_{18}IrN_4O$ (Mol. Wt.: 1047.76): C, 40.12; H, 2.02; N, 5.35. Found: C, 39.89; H, 2.27; N, 5.01. The structure was proven by X-ray analysis.

Iridium, bis[4,6-bis(trifluromethyl)-2-(4-methyl-2-pyridinyl-κN)phenyl-κC],[3-(di-phenylphosphino)-1-propanolato-O,P], (23). 1.0 g (0.0006 mol) of Iridium, di-μ-chlorotetrakis[4,6-bis(trifluromethyl)-2-(4-methyl-2-pyridinyl-κN)phenyl-κC]di-, 0.34 g (0.00148 mol) of 2-diphenylphosphanyl-ethanol 22, 0.60 g (0.0059 mol) of rubidium hydroxide in 5 ml of water, and 40 ml of 1,2-dichloroetane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC], [3-(di-phenylphosphino)-1-propanolato-O,P], was 0.44 g (34%) as yellow solid with no m.p. until 200° C. $^1$H NMR $(CD_2Cl_2)$ 2.30 (s, 6H, Me), 2.35 (br, 1H, CH2-P), 2.35 (br, 1H, CH2-P), 3.80-4.10, (m, 2H, CH2-O), 6.10-8.60 (m, 15H, arom-H). $^{19}$F NMR $(CD_2Cl_2)$ −58.76 (s, 3F, CF3), −60.89 (s, 3F, CF3), −62.57 (s, 3F, CF3), −63.06 (s, 3F, CF3). $^{31}$P NMR $(CD_2Cl_2)$ 11.93. Anal. Calcd. for $C_{42}H_{30}F_{12}IrN_2OP$ (Mol. Wt.: 1029.87): C, 48.98; H, 2.94; N, 2.72. Found: C, 49.10; H, 2.47; N, 3.01. The structure was proven by X-ray analysis.

Iridium, bis[4,6-bis(trifluromethyl)-2-(4-methyl-2-pyridinyl-κN)phenyl-κC],[1-(di-phenylphosphino)-2-propanolato-O,P], (25). 1.0 g (0.0006 mol) of Iridium, di-μ-chlorotetrakis[4,6-bis(trifluromethyl)-2-(4-methyl-2-pyridinyl-κN)phenyl-κC]di-, 0.37 g (0.00151 mol) of 1-diphenylphosphanyl-propan-2-ol 24, 0.60 g (0.0059 mol) of rubidium hydroxide in 5 ml of water, and 40 ml of 1,2-dichloroetane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, bis[4,6-bis(trifluromethyl)-2-(4-methyl-2-pyridinyl-κN)phenyl-κC],[1-(di-phenylphosphino)-2-propanolato-O,P], was 0.87 g (70%) as yellow solid no m.p. until 200° C. $^1$H NMR $(CD_2Cl_2)$ 1.20 (s, 3H, Me), 2.30 (s, 6H, Me), 2.35 (br, 1H, CH2-P), 2.35 (br, 1H, CH2-P), 2.80 (m, 1H, CH2-O), 6.10-8.60 (m, 15H, arom-H). $^{19}$F NMR $(CD_2Cl_2)$ −59.93 (s, 3F, CF3), −60.86 (s, 3F, CF3), −62.63 (s, 3F, CF3), −63.07 (s, 3F, CF3). $^{31}$P NMR $(CD_2Cl_2)$ 9.33. Anal. Calcd. for $C_{43}H_{32}F_{12}IrN_2OP$ (Mol. Wt.: 1043.90): C, 49.47; H, 3.09; N, 2.68. Found: C, 49.53; H, 3.25; N, 2.88. The structure was proven by X-ray analysis.

Iridium, chlorobis[4,6-bis(trifluromethyl)-2-(4-methyl-2-pyridinyl-κN)phenyl-κC],[diphenylphosphine], (27). 1.0 g (0.0006 mol) of Iridium, di-μ-chlorotetrakis[4,6-bis(trifluromethyl)-2-(4-methyl-2-pyridinyl-κN)phenyl-κC]di-, 0.32 g (0.0048 mol) of diphenylphosphanyl-methanol 26, 0.60 g (0.0059 mol) of rubidium hydroxide in 5 ml of water, and 30 ml of 1,2-dichloroetane were refluxed for 2 hours under argon atmosphere. The reaction mixture was poured in the 200 ml of the water and extracted by 200 ml of diethyl ether twice. The extracts were dried over magnesium sulfate overnight. The solvent was removed in rotavapor and residue was purified by chromatography on silica gel with eluent petroleum ether/ethyl ether at 10/0.5. Yield of iridium, chlorobis[4,6-bis(trifluromethyl)-2-(4-methyl-2-pyridinyl-κN)phenyl-κC],[diphenylphosphine], (27) was 0.33 g (27%) as yellow solid with no m.p. until 200° C. $^1$H NMR $(CD_2Cl_2)$ 2.40 (br, 6H, Me), 6.10-8.50 (m, 15H, arom-H). $^{19}$F NMR $(CD_2Cl_2)$ −60.80 (br, 6F, CF3), −63.09 (br, 6F, CF3). $^{31}$P NMR $(CD_2Cl_2)$ −12.11. Anal. Calcd. for $C_{40}H_{27}ClF_{12}IrN_2P$ (Mol. Wt.: 1022.28): C, 47.00; H, 2.66; N, 2.74. Found: C, 47.28; H, 2.70; N, 2.89. The structure was proven by X-ray analysis. Yield of iridium, bis[4,6-bis(trifluromethyl)-2-(4-methyl-2-pyridinyl-κN)phenyl-κC],[1,2-ethanediylbis[diphenylphosphinel]-κP,κP'], chloride (28) was 0.58 g (41%) as yellow solid with no m.p. until 200° C. $^1$H NMR $(CD_2Cl_2)$ 2.40 (br, 6H, Me), 3.10 (br, 4H, CH2-P), 5.90-8.40 (m, 30H, arom-H). $^{19}$F NMR $(CD_2Cl_2)$ −61.37 (br, 6F, CF3), −65.73 (br, 6F, CF3). $^{31}$P NMR $(CD_2Cl_2)$ 23.44. Anal. Calcd. for $C_{54}H_{40}ClF_{12}IrN_2P_2$ (Mol. Wt.: 1234.51): C, 52.54; H, 3.27; N, 2.27. Found: C, 52.73; H, 3.49; N, 2.41. The structure was proven by X-ray analysis.

Iridium, di-μ-hydroxytetrakis[4,6-bis(trifluromethyl)-2-(4-methyl-2-pyridinyl-κN)phenyl-κC]di-, (29). 1.0 g (0.0006 mol) of Iridium, di-μ-chlorotetrakis[4,6-bis(trifluromethyl)-2-(4-methyl-2-pyridinyl-κN)phenyl-κC]di-, 0.35 g (0.0023 mol) of benzoylformic acid, 0.60 g (0.0059 mol) of rubidium hydroxide in 5 ml of water, and 40 ml of 1,2-dichloroetane were refluxed for 2 hours under argon atmosphere. The precipitate was filtered off, washed with 20 ml of water and recrystallized from DMSO. Yield of iridium, di-μ-hydroxytetrakis[4,6-bis(trifluromethyl)-2-(4-methyl-2-pyridinyl-κN)phenyl-κC]di-, was 0.67 g (69%) as yellow solid with no m.p. until 200° C. $^1$H NMR $(CD_2Cl_2)$ 2.60 (br, 6H, Me), 6.10-8.50 (m, 15H, arom-H). $^{19}$F NMR $(CD_2Cl_2)$ −58.97 (br, 6F, CF3), −63.11 (br, 6F, CF3). Anal. Calcd. for $C_{56}H_{34}F_{24}Ir_2N_4O_2$ (Mol. Wt.: 1635.30): C, 41.13; H, 2.10; N, 3.43. Found: C, 41.20; H, 2.10; N, 3.49. The structure was proven by X-ray analysis.

Example 8

OLED devices were fabricated by a thermal evaporation technique. The base vacuum for all of the thin film deposition was in the range of $10^{-6}$ torr. The deposition chamber was capable of depositing eight different films without the need to break up the vacuum.

Patterned indium tin oxide (ITO) coated glass substrates from Thin Film Devices, Inc. were used. These ITOs are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hr.

The cleaned, patterned ITO substrate was then loaded into the vacuum chamber and the chamber was pumped down to $10^{-6}$ torr. The substrate was then further cleaned using an oxygen plasma for about 5 min. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

The OLED samples were characterized by measuring their (1) current-voltage (I-V) curves, (2) electroluminescence radiance versus voltage, and (3) electroluminescence spectra versus voltage The I-V curves were measured with a Source-Measurement Unit (Keithley Model 237, USA). The electroluminescence radiance (in units of $cd/m^2$) vs. voltage was measured with a luminescence meter (Minolta LS-110, Japan), while the voltage was scanned using the Keithley SMU.

The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table I summarizes device configuration and efficiency of OLED devices fabricated using materials disclosed in the present invention. MPMP is the hole-transport material, DPA is the electron-transport material for Emitters 2-4, and DPA/AIQ is the electron-transport material for Emitter 1. AIQ is the electron-injection material. The molecular structures of MPMP, DPA, and ALQ are shown below. The (x,y) color coordinate is based on 1931 convention.

TABLE I

Device configurations and efficiency of OLED devices

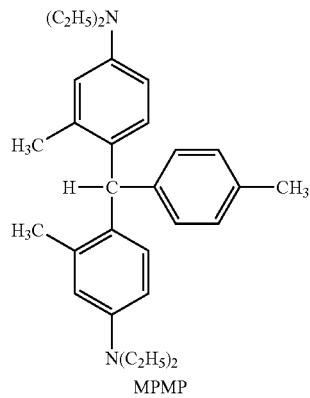
MPMP

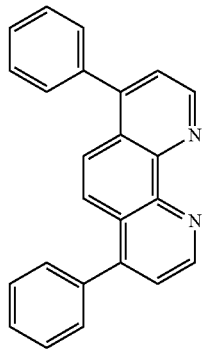
DPA

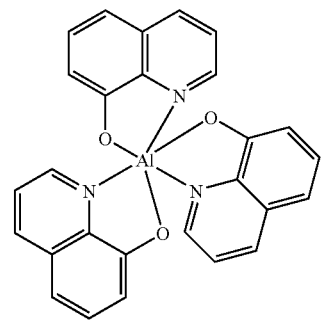
AIQ

| Emitter | Device configuration | Efficiency cd/A | Peak radiance, cd/m2 | Peak wavelength, nm |
|---|---|---|---|---|
| 9 | MPMP(514Å)/emitter 9 (422Å)/DPA(407Å)/ LiF(10Å)/Al(738Å); | 3.5 at 21 V | 350 at 22 V | 470 |
| 12 | MPMP(512Å)/emitter 12(411Å)/DPA(412Å)/ LiF(10Å)/Al(728Å); | 2.5 at 19 V | 420 at 20 V | 470 |
| 17 | MPMP(507Å)/emitter 17(406Å)/DPA(407Å)/ LiF(10Å)/Al(725Å); | 0.03 at 19 V | 3.5 at 19 V | 470 |

TABLE I-continued
Device configurations and efficiency of OLED devices
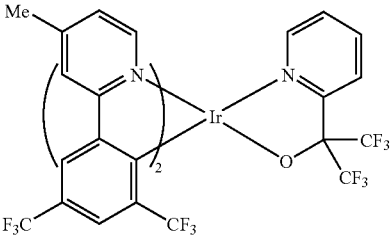
| Emitter | Device configuration | Efficiency cd/A | Peak radiance, cd/m2 | Peak wavelength, nm |
|---|---|---|---|---|
| 19 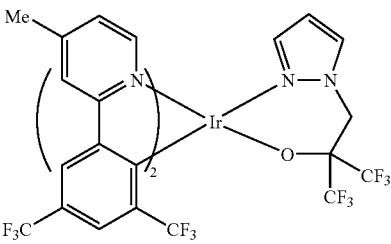 | MPMP(526Å)/emitter 9 (425Å)/DPA(406Å)/ LiF(10Å)/Al(708Å); | 2 at 15 V | 800 at 22 V | 470 |
| 21 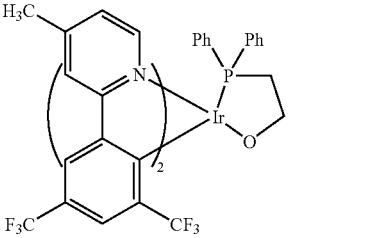 | MPMP(521Å)/emitter 21 (413Å)/DPA(404Å)/ LiF(10Å)/Al(732Å); | 8.5 at 18 V | 1800 at 22 V | 470 |
| 23 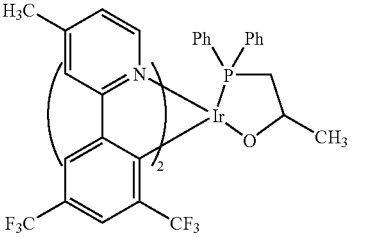 | MPMP(508Å)/emitter 23 (409Å)/DPA(403Å)/ LiF(10Å)/Al(741Å); | 0.6 at 21 V | 60 at 25 V | 470 |
| 25 | MPMP(510Å)/emitter 25(405Å)/DPA(406Å)/Li F(10Å)/Al(726Å); | 2.5 at 17 V | 400 at 22 V | 470 |

TABLE I-continued

Device configurations and efficiency of OLED devices

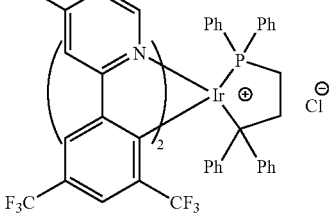

| Emitter | Device configuration | Efficiency cd/A | Peak radiance, cd/m2 | Peak wavelength, nm |
|---|---|---|---|---|
| 28 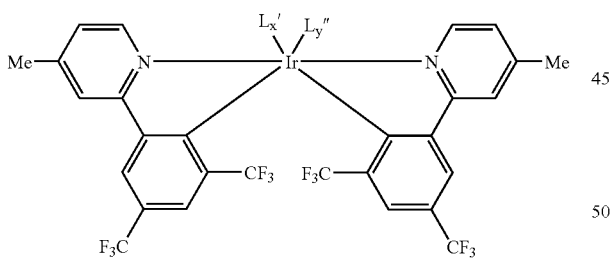 | MPMP(509Å)/emitter 28(409Å)/DPA(409Å)/ LiF(10Å)/Al(735Å); | 1 at 19 V | 30 at 24 V | Signal too weak |

What is claimed is:

1. A composition comprising an iridium complex of the formula:

Formula I

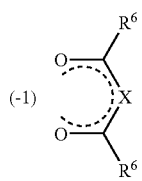

wherein
L' is a bidentate ligand of formula:

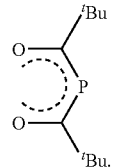
(-1)

where
$R^6$ can be the same or different at each occurrence and is selected from the group of substituted or unsubstituted alkyl, aryl, alkylaryl and heterocyclic groups; x=1, y=0, with the proviso that the iridium is hexacoordinate and in oxidation state 3 and X is a phosphorus or nitrogen atom.

2. The composition of claim 1 wherein bidentate ligand L' has the formula:

(-1)

3. A composition comprising an iridium complex of the formula:

Formula I

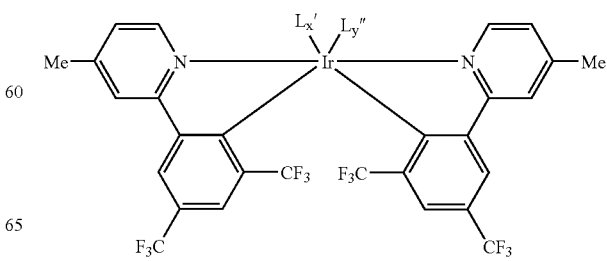

wherein:

L' is a bidentate nitrogen-containing ligand of formula:

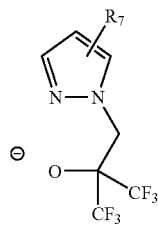

where $R^7$ is a $C_1$ to $C_{12}$ alkyl group or aryl;

x=1, y=0, with the proviso that the iridium is hexacoordinate and in oxidation state 3.

4. The composition of claim 3 wherein bidentate ligand L' has the formula:

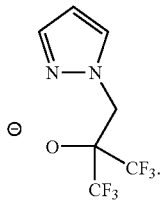

5. A composition comprising an iridium complex of the formula:

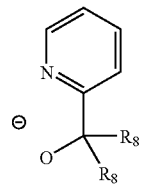

Formula I wherein:

L' is a bidentate nitrogen-containing ligand of formula:

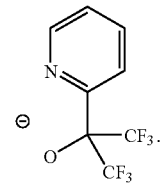

where
$R^8$ can be the same or different at each occurrence and is selected from $CF_3$, $C_2F_5$, n-$C_3F_7$;

x=1, y=0, with the proviso that the iridium is hexacoordinate and in oxidation state 3.

6. The composition of claim 5 wherein bidentate ligand L' has the formula:

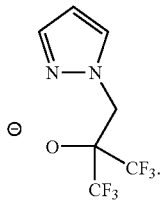

* * * * *